(12) United States Patent
Tegen et al.

(10) Patent No.: US 11,078,176 B2
(45) Date of Patent: Aug. 3, 2021

(54) PUBESCENT PLANT SHALLOW MOVING BED SOLVENT EXTRACTOR AND METHOD OF USE

(71) Applicant: SOCATI TECHNOLOGIES LLC, Seattle, WA (US)

(72) Inventors: Mark Tegen, Austin, TX (US); Oscar Navarro Fernandez, Tigard, OR (US); Joon Hyung Cho, Wilsonville, OR (US); William Rusty Sutterlin, Hoover, AL (US)

(73) Assignee: SOCATI TECHNOLOGIES - OREGON, LLC, Austin, TX (US)

( * ) Notice: Subject to any disclaimer, the term of this patent is extended or adjusted under 35 U.S.C. 154(b) by 0 days.

(21) Appl. No.: 16/588,917

(22) Filed: Sep. 30, 2019

(65) Prior Publication Data
US 2021/0094929 A1    Apr. 1, 2021

(51) Int. Cl.
*B01D 11/02* (2006.01)
*A61K 36/18* (2006.01)
(Continued)

(52) U.S. Cl.
CPC .......... *C07D 309/22* (2013.01); *A61K 36/185* (2013.01); *B01D 11/023* (2013.01); *B01D 11/0269* (2013.01); *B01D 11/0288* (2013.01)

(58) Field of Classification Search
CPC .............. C07D 309/22; B01D 11/0288; B01D 11/0269; B01D 11/0292; B01D 9/0004;
(Continued)

(56) References Cited

U.S. PATENT DOCUMENTS

| 4,266,473 A | 5/1981 | Hunt et al. |
| 5,707,673 A * | 1/1998 | Prevost .................. C11B 1/104 210/634 |

(Continued)

OTHER PUBLICATIONS

Patent Cooperation Treaty, Notification of Transmittal of the International Search Report and the Written Opinion of the International Searching Authority, or the Declaration, FOR-294, dated Mar. 2, 2020, Applicant: Socati Corporation, Authorized Officer: Lee Young.

*Primary Examiner* — Joseph W Drodge
(74) *Attorney, Agent, or Firm* — Flener IP & Business Law; Zareefa B. Flener; Ayhan E. Mertogul (57) ABSTRACT

A shallow bed solvent extractor comprises at least one moving bed having upstream and downstream ends and a feed inlet positioned adjacent to the upstream end, wherein a first batch of wet cannabinoid and terpene containing material is introducible to the at least one moving bed through the feed inlet. An outlet is positioned adjacent to the downstream end, wherein the first batch of wet cannabinoid and terpene containing material is carried on the at least one moving bed and exits the extractor through the outlet. A drive system is operatively connected to the at least one moving bed. The shallow bed solvent extractor further comprises a plurality of sprayers disposed above the upstream and downstream ends of the at least one moving bed and a non-polar solvent. The plurality of sprayers spray the first batch of wet cannabinoid and terpene containing material with the non-polar solvent.

9 Claims, 6 Drawing Sheets

(51) Int. Cl.
*C07D 309/22* (2006.01)
*A61K 36/185* (2006.01)

(58) Field of Classification Search
CPC ... B01D 11/02; B01D 11/0284; B01D 11/023; C07C 37/685; C07C 37/004; C07C 2601/14; C07C 2601/16; C07C 37/68; C07C 37/70; C07C 37/82; C07C 2601/12; A61K 36/00; A61K 36/185; C11B 1/06; C11B 1/10; C11B 1/102; C11B 1/108; C11B 3/001; C11B 3/006; C11B 3/008; C11B 3/16
USPC ........ 554/8, 20, 21, 175, 177; 422/256–259; 424/725, 774; 100/37, 42, 90, 110, 116, 100/118–120, 151, 152
See application file for complete search history.

(56) References Cited

U.S. PATENT DOCUMENTS

| | | | | |
|---|---|---|---|---|
| 8,668,879 B2* | 3/2014 | Kemper | ............... | B01D 11/023 422/261 |
| 10,413,845 B1* | 9/2019 | Tegen | ................... | A61K 36/185 |
| 10,414,709 B1* | 9/2019 | Tegen | ................ | B01D 11/0288 |
| 10,557,105 B1* | 2/2020 | Tran | ......................... | A23L 2/42 |
| 10,799,546 B1* | 10/2020 | Jansen | ................ | C07D 311/78 |
| 10,961,174 B2* | 3/2021 | Tegen | ................... | C07C 37/685 |
| 2006/0283799 A1* | 12/2006 | Homann | .................. | B30B 9/12 210/634 |
| 2013/0022516 A1 | 1/2013 | Kemper et al. | | |
| 2016/0213720 A1* | 7/2016 | Barringer | ............. | A61K 36/185 |
| 2017/0196923 A1* | 7/2017 | Moore | ................... | A23L 19/09 |
| 2017/0252671 A1 | 9/2017 | White et al. | | |
| 2018/0346866 A1* | 12/2018 | Peet | ....................... | C12M 41/40 |
| 2019/0010106 A1 | 1/2019 | Oroskar et al. | | |
| 2019/0077781 A1* | 3/2019 | Dijkstra | ............ | B01D 11/0296 |
| 2019/0224117 A1* | 7/2019 | Shmerlis | ................ | A61K 31/12 |
| 2020/0190002 A1* | 6/2020 | Tegen | ................... | C07C 37/004 |
| 2020/0237840 A1* | 7/2020 | Morrow | ............... | A61K 31/015 |
| 2020/0261404 A1* | 8/2020 | Raz | ....................... | A61K 31/352 |
| 2020/0263109 A1* | 8/2020 | Hansen | ..................... | C11B 1/04 |
| 2020/0281995 A1* | 9/2020 | Lantela | .................. | A61K 31/352 |
| 2020/0306665 A1* | 10/2020 | Mata | ........................ | C07C 37/70 |
| 2020/0398180 A1* | 12/2020 | Hospodor | .......... | B01D 11/0207 |
| 2021/0023155 A1* | 1/2021 | Opperman | ............. | A61K 31/05 |
| 2021/0030824 A1* | 2/2021 | Jansen | ..................... | B01D 3/36 |

* cited by examiner

PUBESCENT PLANT SHALLOW MOVING BED SOLVENT EXTRACTOR AND METHOD OF USE

FIELD OF THE INVENTION

This invention relates generally to equipment and a method for use thereof in the extraction of cannabinoids and terpenes from pubescent plant matter using an organic solvent, and in particular to equipment and a method for use thereof in the extraction of cannabinoids and terpenes from pubescent plant matter using a non-polar organic solvent.

BACKGROUND

The production of an extract concentrate from plant matter, for example without limitation hemp and/or *Cannabis*, starts with the mechanical preparation of the plant matter. Mechanical preparation comprises drying, removal of the stalk and stems, and size reduction of the remaining flower and leaf material by grinding to generate a high surface area extractable material. The so prepared hemp and/or *Cannabis* material is then transferred from the preparation equipment to the solvent extraction equipment where it is treated with an organic solvent, for example without limitation ethanol, compressed butane, hexane, or super critical carbon dioxide to solvent extract the cannabinoids.

For the solvent extraction of the *Cannabis* and/or hemp plant material, the hemp and/or *Cannabis* material is first dried to roughly 10% moisture. The dried material is then separated into two fractions, flower and leaf material and stem and stalk material. The dried flower and leaf material is then subject to, for example, one of three main types of extraction methods.

A first exemplary extraction method is the so-called butane hash oil (BHO) extraction method which involves loading a cylinder with the dried flower and leaf material. The cylinder is then connected to a device that pumps a volume of compressed butane liquid through the cylinder and into a collection tank. Cannabinoids and plant oils are washed out of the dried flower and leaf in the cylinder and into the collection tank. The resulting butane liquid and cannabinoid extract solution is then processed to allow for the evaporation of the butane, which is subsequently captured and re-compressed for re-use. The remaining extracted cannabinoid oil (or hash oil) is then taken through additional processing steps to remove lipids, waxes, and other plant materials.

A second exemplary extraction method is the so-called cold ethanol extraction process, which also involves loading a cylinder with the dried flower and leaf material. The cylinder is then connected to a device that pumps, sprays, and/or draws a volume of ethanol having a temperature in the range of about −20° C. to about −10° C. through the cylinder. Cannabinoids and plant oils are washed out of the dried flower and leaf contained in the cylinder and into a collection vessel. Typically, the extracted solution of ethanol and cannabinoids is filtered in its "chilled" state whereby any dissolved waxes are removed from the extract liquor by crystallization or winterization. The ethanol is then evaporated from the extract cannabinoids and any remaining plant waxes or lipids. The ethanol is collected and re-used. The remaining extracted cannabinoid oil (or hash oil) is then taken through additional processing steps to remove residual solvents.

A third exemplary extraction method is the so-called super critical carbon dioxide method, which again involves loading a cylinder with the dried flower and leaf material. The cylinder is then connected to a device that pumps a volume of highly compressed carbon dioxide through the cylinder. The carbon dioxide ($CO_2$) is compressed to a point equal to or above its critical point where the resulting $CO_2$ has the density of a liquid and the diffusive nature of a gas, thereby extracting the cannabinoids, terpenes, lipids, and other extractable plant matter. The extracted solution then flows to a collection tank where the $CO_2$ is allowed to "de-gas" from the extracted liquid of cannabinoids and other plant matter, and is released or recompressed for re-use. The remaining extracted cannabinoid oil (or hash oil) is then taken through additional processing steps to remove lipids, waxes, and other plant matter.

Known methods of extraction in the art typically involve hand harvesting of field grown hemp to minimize the capture of stalk and stem material. The flower material of the hand harvested plants is then dried from about 70% moisture to about 10% moisture. Once the drying is complete the flower material is separated from the remaining stalk and stem material by hand to concentrate the flower material in its dried form. All the known methods in the art involve significant labor costs associated with the hand harvesting and processing in addition to the energy intensive drying of the plant matter from typically about 70% moisture to about 10% moisture. It is difficult to see how the industry can evolve efficiently if thousands of acres of hemp are to be harvested and processed by hand in addition to the significant cost of drying the plant matter. Therefore, there is a need for methods and devices that allow for the extraction of cannabinoids, terpenes, and other plant materials from whole plant, wet, and in a continuous system that allows for the use of modern farm processing equipment.

SUMMARY OF THE INVENTION

According to one aspect of the invention, a shallow bed solvent extractor comprises at least one moving bed having upstream and downstream ends and a feed inlet positioned adjacent to the upstream end, wherein a first batch of wet cannabinoid and terpene containing material is introducible to the at least one moving bed through the feed inlet. An outlet is positioned adjacent to the downstream end, wherein the first batch of wet cannabinoid and terpene containing material is carried on the at least one moving bed and exits the extractor through the outlet. A drive system is operatively connected to the at least one moving bed. The shallow bed solvent extractor further comprises a plurality of sprayers disposed above the upstream and downstream ends of the at least one moving bed and a non-polar solvent. The plurality of sprayers spray the first batch of wet cannabinoid and terpene containing material with the non-polar solvent.

According to another aspect of the invention, a shallow bed solvent extractor comprises at least one moving bed having upstream and downstream ends and a feed inlet positioned adjacent to the upstream end, wherein a first batch of wet cannabinoid and terpene containing material is introducible to the at least one moving bed through the feed inlet. An outlet is positioned adjacent to the downstream end, wherein the first batch of wet cannabinoid and terpene containing material is carried on the at least one moving bed and exits the extractor through the outlet. A drive system is operatively connected to the at least one moving bed. The shallow bed solvent extractor further comprises a plurality of sprayers disposed above the upstream and downstream ends of the at least one moving bed and a pressing mechanism operationally disposed under the outlet, wherein the wet cannabinoid and terpene containing material exits the extractor through the outlet and is introduced into the pressing mechanism.

According to a further aspect of the invention, a method for using a shallow bed solvent extractor, comprises the steps of providing a shallow bed solvent extractor comprising at least one moving bed having upstream and downstream ends, a feed inlet positioned adjacent to the upstream end, an outlet positioned adjacent to the downstream end, a non-polar solvent, a drive system operatively connected to the at least one moving bed, and a plurality of sprayers disposed above the upstream and downstream ends of the at least one moving bed. The method further comprises the steps of introducing a first batch of wet cannabinoid and terpene containing material into the at least one moving bed through the feed inlet, carrying the first batch of wet cannabinoid and terpene containing material on the at least one moving bed, and washing the first batch of wet cannabinoid and terpene containing material being carried on the at least one moving bed with the non-polar solvent sprayed through the plurality of sprayers.

BRIEF DESCRIPTION OF THE DRAWINGS

The above mentioned and other features of this invention will become more apparent and the invention itself will be better understood by reference to the following description of embodiments of the invention taken in conjunction with the accompanying drawings, wherein.

Other aspects and advantages of the present invention will become apparent upon consideration of the following detailed description, wherein similar structures have similar reference numerals.

DETAILED DESCRIPTION

The invention will now be described in the following detailed description with reference to the drawings, wherein preferred embodiments are described in detail to enable practice of the invention. Although the invention is described with reference to these specific preferred embodiments, it will be understood that the invention is not limited to these preferred embodiments. But to the contrary, the invention includes numerous alternatives, modifications and equivalents as will become apparent from consideration of the following detailed description.

Approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In at least some instances, the approximating language may correspond to the precision of an instrument for measuring the value. Range limitations may be combined and/or interchanged, and such ranges are identified and include all the sub-ranges included herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about."

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present. As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements, but may include other elements not expressly listed or inherent to such process, method, article, or apparatus. The singular forms "a," "an," and "the" include plural referents unless the context clearly dictates otherwise.

Shallow moving bed solvent extractors are known in the art. For example, FIGS. 1 and 2 taken from U.S. Pat. No. 8,668,879, which is incorporated by reference herein in its entirety, illustrate an example of such an extractor that includes a housing (12) having two oppositely moving beds upon which a cannabinoid and terpene containing hemp and/or *Cannabis* material may be exposed to a solvent for extraction.

It the instant invention, the hemp and/or *Cannabis* material is exposed to the solvent in its whole plant wet form, or in a silage chopped whole plant wet form, or as a mixture of one or more of silage chopped material, separated flower in its wet form, and dried cannabinoid and terpene containing material. In one embodiment, the hemp and/or *Cannabis* material is extracted or washed with a non-polar organic solvent such as but not limited to a terpene such as, for example, d'limonene, Myrcene, Linalool, Caryophyllene, Alpha-pinene, Beta-pinene, Humulene, and combinations thereof.

In another embodiment a polar solvent comprising but not limited to ethanol or other alcohols such as butanol can be mixed with a non-polar solvent such as a terpene or n-hexane. In a further embodiment a polar solvent comprising but not limited to ethanol or butanol is used.

Figure 1:
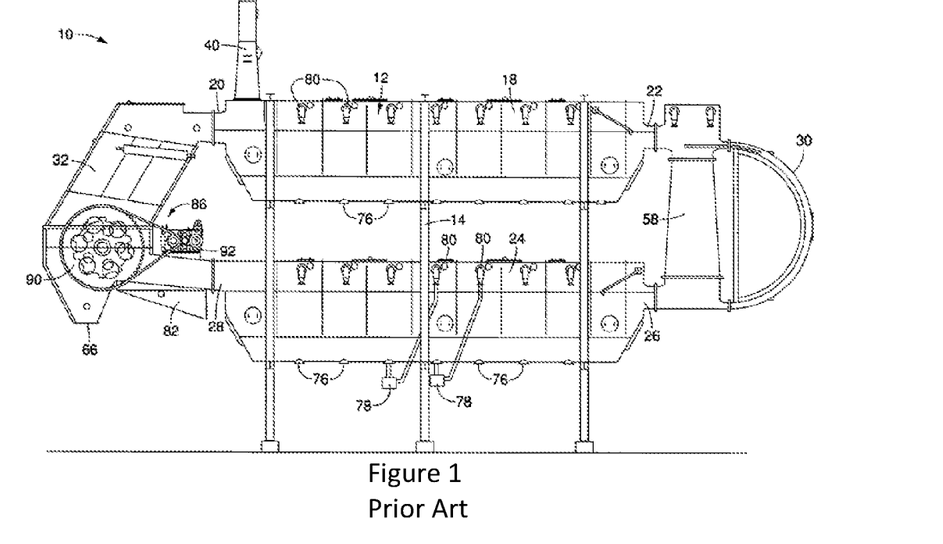
FIG. 1 is a side view of an exemplary prior art shallow moving bed solvent extractor having upper and lower oppositely moving beds.

As is disclosed in U.S. Pat. No. 8,668,879, the exemplary shallow moving bed solvent extractor includes upper and lower oppositely moving beds (18, 24), where an upstream end (20) of the upper bed (18) is positioned over a downstream end (28) of the lower bed (20), and a downstream end (22) of the upper bed (18) is disposed over an upstream end (26) of the lower bed (24). The upper and lower beds (18, 20) are connected, for example, by an elbow (30) that connects the downstream end (22) of the upper bed (18) to the upstream end (26) of the lower bed (24).

The shallow moving bed solvent extractor need not have two moving beds as illustrated in U.S. Pat. No. 8,668,879. For the purposes of the instant invention a single moving bed is all that is required. For example, the extractor may comprise only the upper bed (18) or the lower bed (24).

Figure 2:
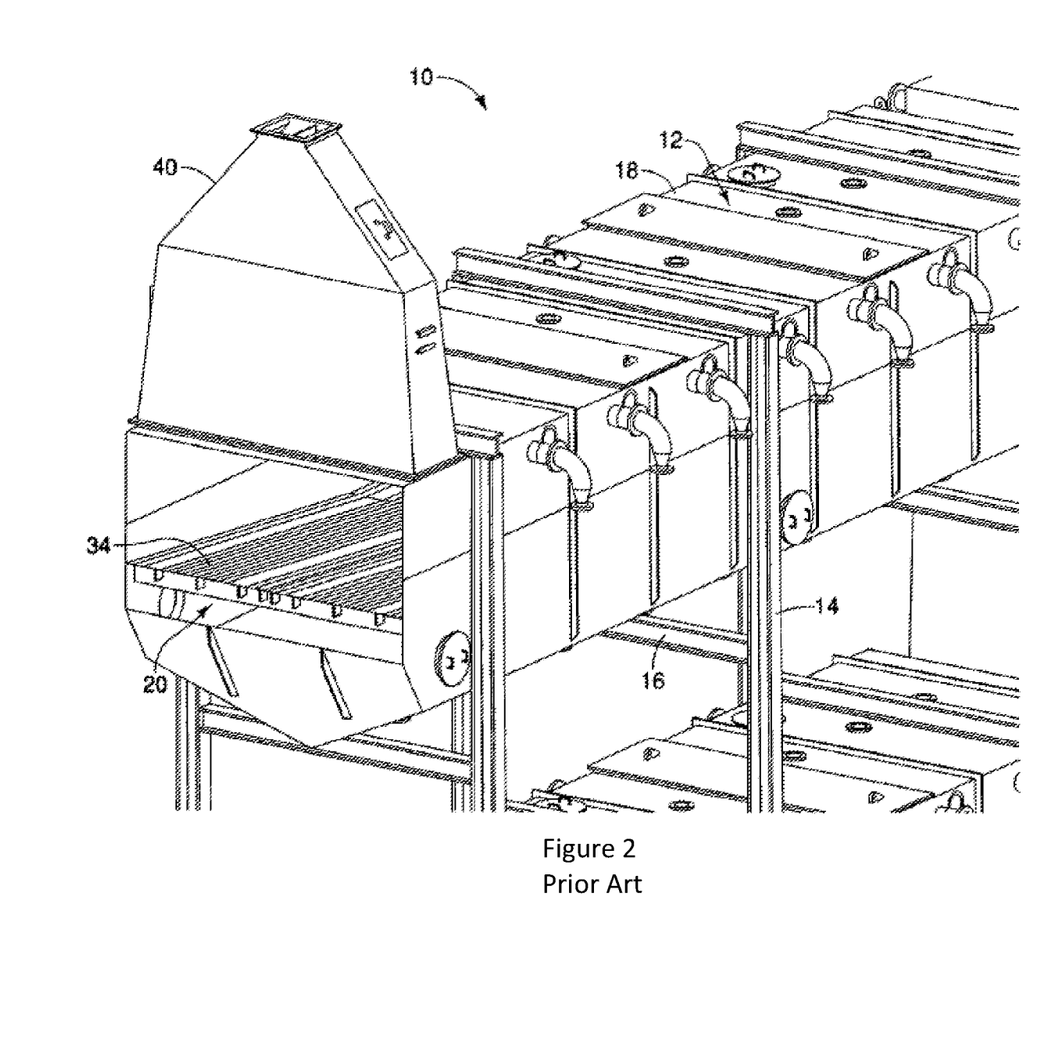
FIG. 2 is a perspective close up view of a feed inlet positioned over an upstream end of the upper bed of an exemplary prior art shallow moving bed solvent extractor having upper and lower oppositely moving beds.

Referring to FIG. 2, in one embodiment, a feed inlet (40) is positioned over the upstream end (20) of a floor (34) of the upper bed (18). Wet cannabinoid and terpene containing material is input into the shallow moving bed solvent extractor, for example, through the feed inlet (40) and spread over the floor (34) of the upper bed (18). The wet cannabinoid and terpene containing material travels with the upper bed (18) and is washed from above with solvent, for example, via a series of sprayers (for example, see reference numeral 80 in FIG. 3 of U.S. Pat. No. 8,668,879) that are arranged over the upper and lower beds (18, 24).

Figure 4:
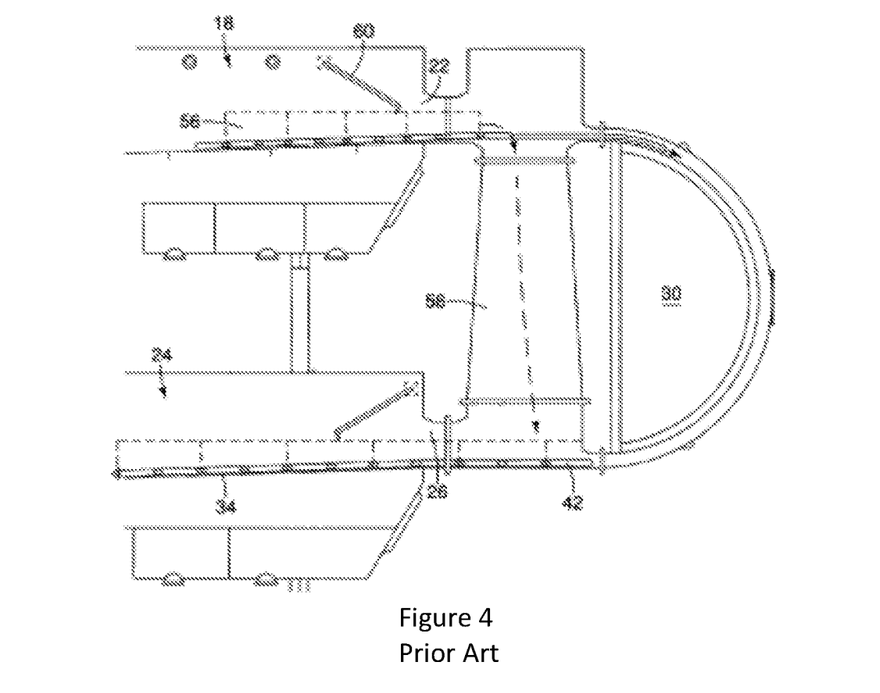
FIG. 4 is a side view of a chute and elbow connecting the upper and lower oppositely moving beds of an exemplary prior art shallow moving bed solvent extractor.

After traveling the length of the upper bed (18), the wet cannabinoid and terpene containing material travels from the downstream end (22) of the upper bed (18) to the upstream end (26) of the floor (34) of the lower bed (24), for example as illustrated in FIG. 4, via a chute 58. The chute 58 is configured to allow the wet cannabinoid and terpene containing material to be transferred from the upper bed (18) to the lower bed (24), for example, without having to push the material through the elbow (30). The wet cannabinoid and terpene containing material travels with the lower bed (24) and is again washed from above with the solvent via the series of sprayers (80). After traveling the length of the lower bed (20), the wet cannabinoid and terpene containing material exits the shallow moving bed solvent extractor through an outlet thereon, for example, outlet (66) illustrated in FIG. 1 near to the downstream end (28) of the lower bed (24).

Figure 1A:
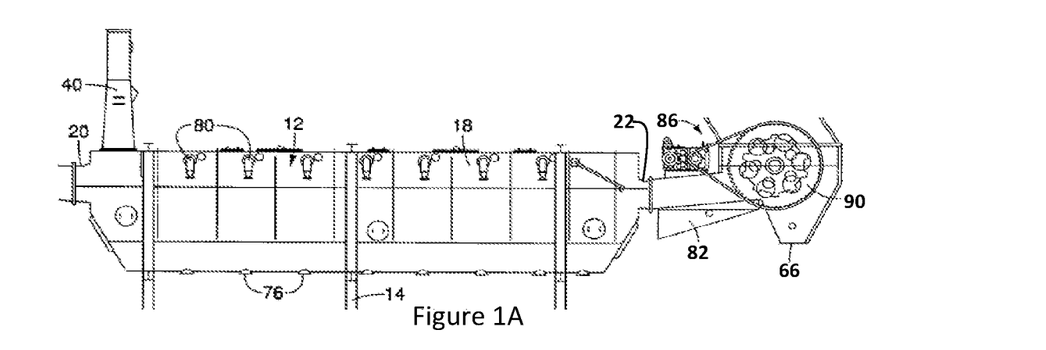
FIG. 1A is a side view of an exemplary prior art shallow moving bed solvent extractor having a single moving bed.

Referring to FIG. 1A, an embodiment the shallow moving bed solvent extractor comprises a single moving bed (18) having a feed inlet (40) positioned over the upstream end (20) of the single moving bed (18). After traveling the length of the single moving bed (18) the wet cannabinoid and terpene containing material exits the shallow moving bed solvent extractor through the outlet (66) thereon near to the downstream end (22) of the single moving bed (18). Except for the differences in the geometry of two moving beds versus one moving bed, and the resultant elimination of the elbow (30) and the chute (58), the structure and operation of the single bed embodiment of the shallow moving bed solvent extractor shown in FIG. 1A is otherwise the same as the structure and operation of the two moving bed solvent extractor shown in FIG. 1.

Figure 3:
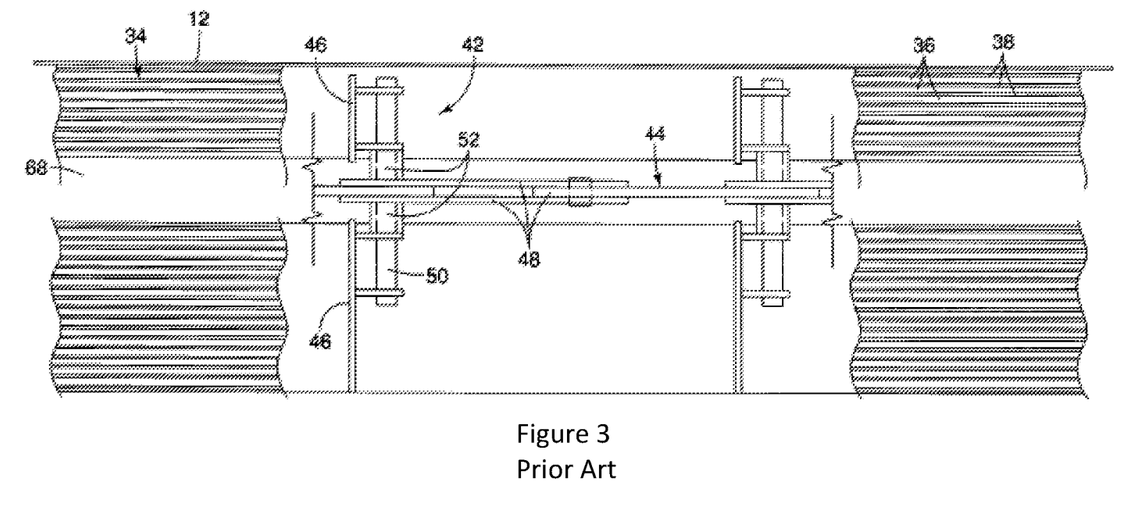
FIG. 3 is a top plan view of a floor of a moving bed of an exemplary prior art shallow moving bed solvent extractor.

Referring to FIG. 3 (originally FIG. 6 of U.S. Pat. No. 8,668,879), each of the upper and lower beds (18, 24) includes the floor (34) extending the length thereof between the upstream ends (20, 26) and the downstream ends (22, 28) of the respective bed. Each floor (34) is constructed to include openings disposed therethrough. For example as illustrated in FIG. 3, the openings may be gaps (38) disposed between bars (36) that comprise the beds (18, 24). The beds (18, 24) may comprise structures other than bars (36) and openings disposed therethrough other than the gaps (38) as is known in the art. Regardless of the particular structure of the floor (34) or the beds (18, 24), or the particular form of the openings, the openings are sized and configured to allow the solvent to pass through each floor (34). The solvent passing through each floor (34), now rich in cannabinoids and terpenes extracted from the washed material, is collected beneath the floor (34).

It is generally understood that a portion of the wet cannabinoid and terpene containing material being washed by the solvent will be entrained by the solvent and fall through the openings. In one embodiment, when the cannabinoid and terpene rich solvent is collected beneath one section of the floor (34), the solvent is redirected to be sprayed onto the wet cannabinoid and terpene containing material upstream from the one section so that any entrained material is added to the wet cannabinoid and terpene containing material upstream from where the entrained material fell through the floor (34).

Figure 5:
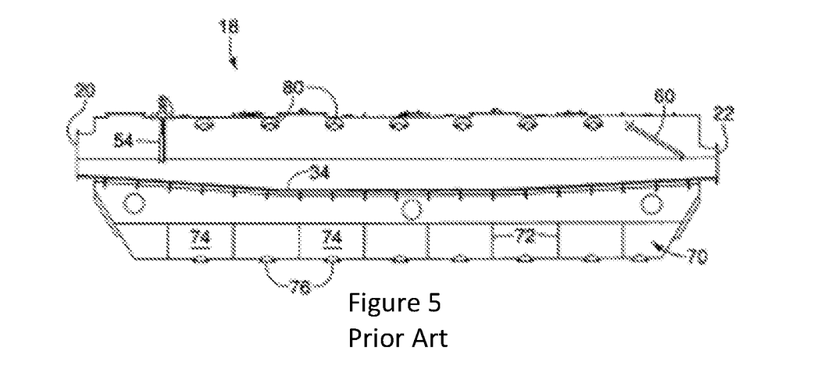
FIG. 5 is a side view of a trough of a moving bed of an exemplary prior art shallow moving bed solvent extractor.

The cannabinoid and terpene rich solvent that falls through the openings of the floor (34) of each of the upper and lower beds (18, 24) is collected therebelow, for example, by a trough (70) illustrated for the upper bed (18) in FIG. 5 (originally FIG. 3 of U.S. Pat. No. 8,668,879). In one embodiment each trough (70) has an elongated structure that extends between the upstream (20, 26) and downstream (22, 28) ends of the upper and lower beds (18, 24). The troughs (70) can have any cross-sectional shape and can be arranged at any orientation sufficient to receive the cannabinoid and terpene rich solvent from the wet cannabinoid and terpene containing material above. In one embodiment, each trough (70) is separated into individual hoppers (74) distributed along the length of the trough (70).

Referring to FIGS. 1 and 5, the concentration of extracted cannabinoids to solvent increases from a smaller cannabinoid to solvent ratio collected in the hopper (74) closest to the downstream end (28) of the lower bed (24) to a larger cannabinoid to solvent ratio collected in the hopper (74) closest to the upstream end (20) of the upper bed (18). In the single moving bed embodiment illustrated in FIG. 1A, the concentration of extracted cannabinoids to solvent increases from a smaller cannabinoid to solvent ratio collected in the hopper (74) closest to the downstream end (22) of the single moving bed (18) to a larger cannabinoid to solvent ratio collected in the hopper (74) closest to the upstream end (20) of the single moving bed (18).

Clean solvent and the cannabinoid and terpene rich solvent are sprayed onto the wet cannabinoid and terpene containing material in a counter-current manner as the wet material travels along the upper and lower beds (18, 24) in one embodiment, or along the single moving bed (18) in another embodiment. For example, in one embodiment, each circulating pump (76) is operatively connected to the sprayer (80) located immediately upstream therefrom. In another embodiment, the sprayer (80) immediately upstream from the downstream end (28) of the lower bed (24) is configured to spray clean solvent onto the wet cannabinoid and terpene containing material therebelow, whereas the sprayer (80) immediately downstream from the upstream end (20) of the upper bed (18) is configured to spray solvent having the highest concentration of cannabinoids to solvent ratio onto the wet cannabinoid and terpene containing material therebelow. In a further embodiment, the sprayer (80) immediately upstream from the downstream end (22) of the single moving bed (18) is configured to spray clean solvent onto the wet cannabinoid and terpene containing material therebelow, whereas the sprayer (80) immediately downstream from the upstream end (20) of the single moving bed (18) is configured to spray solvent having the highest concentration of cannabinoids to solvent ratio onto the wet cannabinoid and terpene containing material therebelow. This counter-current manner of spraying aides in removing the maximum amount of cannabinoids from the wet cannabinoid and terpene containing material because the clean solvent should be more effective at removing any remaining cannabinoids at the end of the cycle than at the beginning. Additional details regarding the structure and operation of a shallow moving bed solvent extractor including, for example, drive mechanisms for the one or more moving beds (18, 24), structure of the troughs (70), the components for collecting and recirculating the solvent, and other structural features are disclosed in U.S. Pat. No. 8,668,879, or are otherwise known to those having ordinary skill in the art.

In one embodiment the clean solvent used in the extraction comprises a terpene previously extracted from the wet cannabinoid and terpene containing material. When used as at least a portion of the solvent sprayed onto the wet cannabinoid and terpene containing material, the previously extracted terpene extracts not only the cannabinoids but also additional terpenes therefrom. Following an extraction process using a shallow moving bed solvent extractor as described hereinabove, the wet material contains lower concentrations of cannabinoids and terpenes than before the extraction process. However, despite the concentrations being lower, useful levels of cannabinoids and terpenes may remain. Therefore, the post extraction wet material is introduced into a pressing mechanism, for example without limitation, a screw press, a jacketed screw press, a sludge press, or another type of press as is known in the art.

Figure 6:
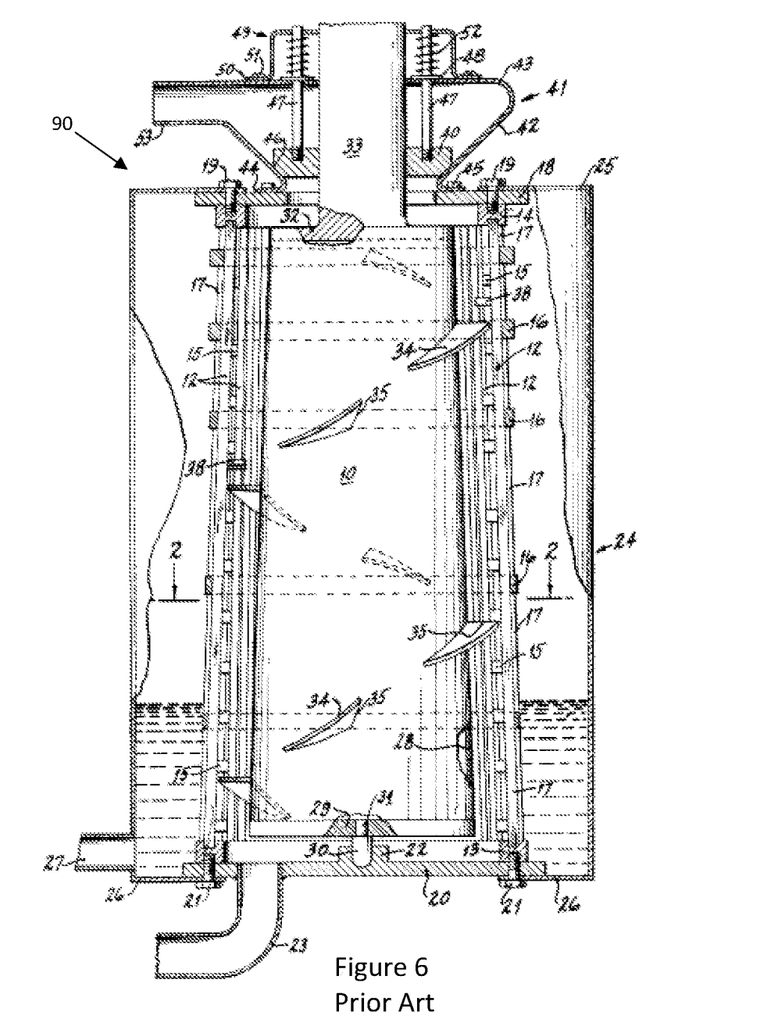
FIG. 6 is a prior art exemplary pressing mechanism for use with a shallow moving bed solvent extractor.

FIG. 6 taken from U.S. Pat. No. 2,960,926, which is incorporated by reference herein in its entirety, illustrates an exemplary pressing mechanism 90, for example, a jacketed screw press. Because the exemplary pressing mechanism 90 shown in FIG. 6 was taken from a prior art reference it includes reference numerals that are, with the exception of identifying reference numeral 90, particular to FIG. 6 alone and that should not be compared with or applied to other figures or other portions of the current application outside of this paragraph. The exemplary pressing mechanism 90 shown in FIG. 6 is described as receiving a pulp suspension, for example, the post extraction wet material, of about 2% pulp and about 98% water in conduit 23. Flights 34 and 35 rotating on spindle 11 push the pulp suspension upwardly while squeezing out water that collects as shown at a lower part of the outer shell 24. In the context of the current invention, the post extraction wet material would get pushed upwardly while absorbed solvent, for example, terpenes, along with some water/organic matter would be collected at the lower part of the shell 24. In the exemplary pressing mechanism 90 shown in FIG. 6, the pulp suspension at a top of the exemplary pressing mechanism 90 near the collar 40 is disclosed be about 40% pulp and about 60% water. Thus the exemplary pressing mechanism 90 presses out nearly half of the water in the pulp suspension entering at conduit 23; however, in the context of the current invention these percentages are exemplary only and not meant to be limiting in any way.

Figure 7:
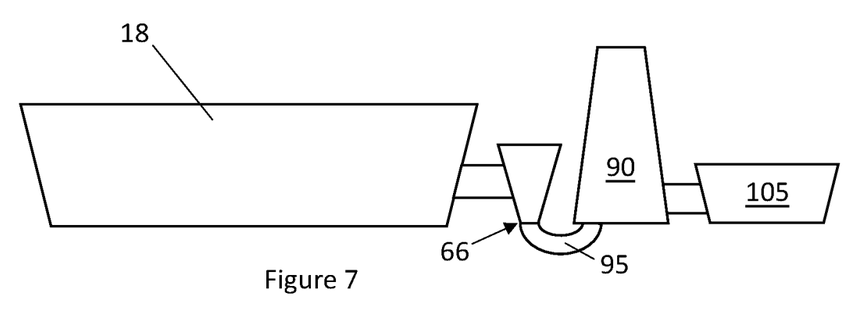
FIG. 7 is a schematic side view of a collection vessel and an exemplary pressing mechanism connected for use with a shallow moving bed solvent extractor having a single moving bed.
Figure 7A:
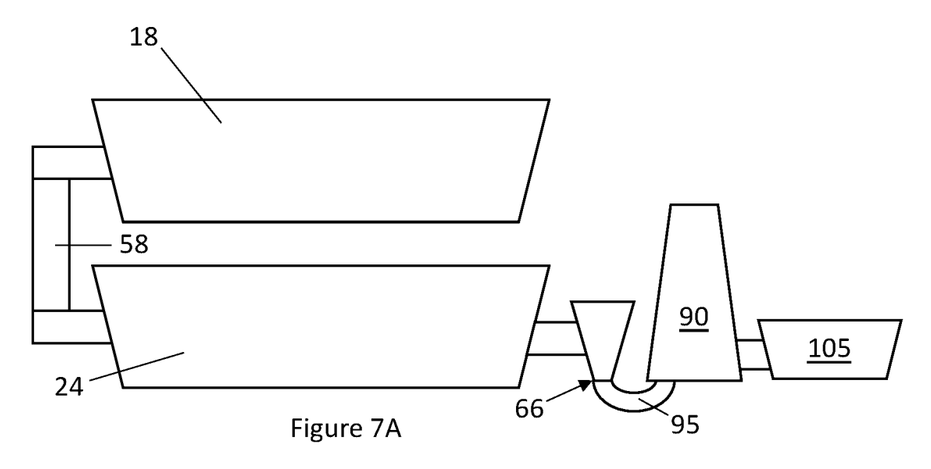
FIG. 7A is a schematic side view of a collection vessel and an exemplary pressing mechanism connected for use with a shallow moving bed solvent extractor having upper and lower oppositely moving beds.

As illustrated schematically in FIGS. 7 and 7A, the pressing mechanism 90 is operationally disposed under the outlet (66) of either of the single (18) or multiple (18, 24) moving bed solvent extractors described hereinabove. The wet cannabinoid and terpene containing material exits the outlet (66) and is introduced into the pressing mechanism 90, for example, through a conduit 95. Upon introduction into the pressing mechanism 90, the wet cannabinoid and terpene containing material is compressed by the pressing mechanism 90 to squeeze out any absorbed solvent, for example, terpenes, along with some water/organic matter.

The squeezed out materials are collected, for example, in a collection vessel 105, mixed with water, and allowed to stand until the mixture separates into solvent, for example, terpenes, and other materials. In one embodiment the mixture of the squeezed out materials and water is allowed to stand for between about 0.1 hour and about 100 hours at between about 5° C. and about 90° C., and between about 0.1 bar pressure and about 5 bar pressure until the solvent separates out of the mixture. In other embodiments the mixture of squeezed out materials and water is allowed to stand for other times, and/or at other temperatures, and/or under other pressures. The separated solvent, for example, terpenes, is collected and used as clean solvent in a subsequent extraction process.

INDUSTRIAL APPLICABILITY

The shallow bed solvent extractor extracts terpenes from wet cannabinoid and terpene containing material. The wet cannabinoid and terpene containing material that passes through the extractor is introduced into a pressing mechanism where the material gets compressed by the pressing mechanism to squeeze out any absorbed solvent along with some water/organic matter.

The squeezed out materials are collected, mixed with water, and allowed to stand until the mixture separates into solvent and other materials. The separated solvent is collected and used as clean solvent in a subsequent extraction process. The shallow bed solvent extractor can be used in industry, particularly in the processing of wet cannabinoid and terpene containing material.

Numerous modifications to the present invention will be apparent to those skilled in the art in view of the foregoing description. It is not desired to limit the invention to the exact construction and operation shown and described, and accordingly, all suitable modifications and equivalents may be resorted to, falling within the scope of the invention. Accordingly, this description is to be construed as illustrative only of the principles of the invention and is presented for the purpose of enabling those skilled in the art to make and use the invention and to teach the best mode of carrying out same. The exclusive rights to all modifications which come within the scope of the appended claims are reserved. All patents, patent publications and applications, and other references cited herein are incorporated by reference herein in their entirety.

We claim:

1. A shallow bed solvent extractor comprising:
   at least one moving bed having upstream and downstream ends;
   a feed inlet positioned adjacent to the upstream end, wherein a first batch of wet cannabinoid and terpene containing material is introducible to the at least one moving bed through the feed inlet;
   an outlet positioned adjacent to the downstream end, wherein the first batch of wet cannabinoid and terpene containing material is carried on the at least one moving bed and exits the extractor through the outlet; and
   a drive system operatively connected to the at least one moving bed;
   a plurality of sprayers disposed above the upstream and downstream ends of the at least one moving bed; and
   a terpene solvent; wherein
   the plurality of sprayers spray the first batch of wet cannabinoid and terpene containing material with the terpene solvent; and wherein the shallow bed extractor further comprises:
a pressing mechanism operationally disposed downstream of the outlet, wherein the wet cannabinoid and terpene containing material exits the extractor through the outlet and is introduced into the pressing mechanism, and the pressing mechanism is configured to compress the wet cannabinoid and terpene containing material and to squeeze out a mixture of one or more terpenes, water, and other organic matter from the wet cannabinoid and terpene containing material; and
a collection vessel connected directly to the pressing mechanism and configured to collect the squeezed out mixture of one or more terpenes, water, and other organic matter, wherein the collection vessel is further configured to allow the squeezed out mixture of one or more terpenes, water, and other organic matter to stand until the squeezed out one or more terpenes separates out of the mixture; and wherein
at least a portion of the terpene solvent comprises the squeezed out one or more terpenes separated out of the mixture.

2. The shallow bed solvent extractor of claim 1, wherein the terpene solvent is selected from the group of terpenes consisting of d'limonene, Myrcene, Linalool, Caryophyllene, Alpha-pinene, Beta-pinene, Humulene, and combinations thereof.

3. The shallow bed solvent extractor of claim 1, wherein at least a portion of the terpene solvent is extracted from a second batch of wet cannabinoid and terpene containing material introduced into the shallow bed solvent extractor prior to the introduction of the first batch.

4. The shallow bed solvent extractor of claim 1, wherein the at least one moving bed comprises two oppositely moving beds operationally connected between the downstream end of the first moving bed and the upstream end of the second moving bed.

5. The shallow bed solvent extractor of claim 1, wherein the pressing mechanism is selected from the group of pressing mechanisms consisting of a screw press, a jacketed screw press, and a sludge press.

6. A method for using a shallow bed solvent extractor, comprising the steps of:
providing a shallow bed solvent extractor comprising:
at least one moving bed having upstream and downstream ends;
a feed inlet positioned adjacent to the upstream end;
an outlet positioned adjacent to the downstream end;
a terpene solvent;
a drive system operatively connected to the at least one moving bed; and
a plurality of sprayers disposed above the upstream and downstream ends of the at least one moving bed;
introducing a first batch of wet cannabinoid and terpene containing material into the at least one moving bed through the feed inlet;
carrying the first batch of wet cannabinoid and terpene containing material on the at least one moving bed;
washing the first batch of wet cannabinoid and terpene containing material being carried on the at least one moving bed with the terpene solvent sprayed through the plurality of sprayers;
providing a pressing mechanism operationally disposed downstream of the outlet:
allowing the wet cannabinoid and terpene containing material to exit the extractor through the outlet;
introducing the wet cannabinoid and terpene containing material into the pressing mechanism;
compressing the wet cannabinoid and terpene containing material within the pressing mechanism to squeeze out a mixture of one or more terpenes, water, and other organic matter from the wet cannabinoid and terpene containing material;
collecting the mixture of one or more terpenes, water, and other organic matter;
allowing the mixture of one or more terpenes, water, and other organic matter to stand until the one or more terpenes separates out of the mixture; and
collecting the one or more terpenes and using the one or more collected terpenes as part of the terpene solvent in the washing step.

7. The method for using a shallow bed solvent extractor of claim 6, wherein at least a portion of the terpene solvent is extracted from a second batch of wet cannabinoid and terpene containing material introduced into the shallow bed solvent extractor prior to the introduction of the first batch.

8. The method for using a shallow bed solvent extractor of claim 6,
wherein the mixture of one or more terpenes, water, and other organic matter is allowed, to stand for between about 0.1 hour and about 100 hours at between about 5° C. and about 90° C., and between about 0.1 bar pressure and about 5 bar pressure until the one or more terpenes separates out of the mixture.

9. The method for using a shallow bed solvent extractor of claim 6, wherein the terpene solvent is selected from the group of terpenes consisting of d'limonene, Myrcene, Linalool, Caryophyllene, Alpha-pinene, Beta-pinene, Humulene, and combinations thereof.

* * * * *